United States Patent [19]

Bauer

[11] 4,235,685

[45] Nov. 25, 1980

[54] PREPARATION OF 3-THENYL BROMIDE

[75] Inventor: Dennis P. Bauer, Baton Rouge, La.

[73] Assignee: Ethyl Corporation, Richmond, Va.

[21] Appl. No.: 71,993

[22] Filed: Sep. 4, 1979

[51] Int. Cl.² .................................................. B01J 1/10
[52] U.S. Cl. ............................................... 204/158 HA
[58] Field of Search ................................... 204/158 HA

[56] References Cited

U.S. PATENT DOCUMENTS 3,947,336   3/1976   Clarke et al. ................ 204/158 HA

*Primary Examiner*—Howard S. Williams
*Attorney, Agent, or Firm*—Donald L. Johnson; John F. Sieberth; James M. Pelton

[57] ABSTRACT

A process for selective bromination of alkyl heterocyclic compounds, such as alkyl thiophenes, by reacting with a brominating agent in a solvent using infrared light as an initiator.

17 Claims, No Drawings

PREPARATION OF 3-THENYL BROMIDE

BACKGROUND OF THE INVENTION

This invention relates to a process for brominating aromatic compounds, particularly thiophene compounds. More specifically, this invention relates to a process for selectively brominating the alkyl side-chain of 3-alkyl thiophenes.

Thiophenes have considerable interest as intermediates for pharmaceutical compounds, particularly amino acid antagonists, in vasopressor action and intermediates for antibacterial semisynthetic penicillin and cephalosporin compounds, particularly Ticarcillin.

In view of such interest, any number of methods have been described in the chemical literature for the preparation of brominated aromatic compounds. Particularly, brominated alkyl thiophenes, described in Campaigne et al, *J. Amer. Chem. Soc.*, Vol. 70, pp. 1555–1558 (1948), are prepared by reacting 3-methylthiophene with N-bromosuccinimide in the presence of a benzoyl peroxide initiator. The 3-thenyl bromide was subsequently used for preparation of other thiophene compounds. Selectivity of reaction on the methyl side-chain was much increased by the use of benzoyl peroxide as an initiator. Dittmer et al, *J. Amer. Chem. Soc.*, Vol. 71, pp. 1201–1204 (1949), teaches that excess brominating agent, such as 2 moles of N-bromosuccinimide per mole of 2- or 3-methylthiophene will give dibrominated thiophenes even in the presence of a directing benzoyl peroxide initiator. One mole of brominating agent per mole of 2- or 3-methylthiophene gives predominately side-chain brominated methylthiophene in the presence of benzoyl peroxide initiator. The preparation of 3-thenyl bromide from 3-methylthiophene using benzoyl peroxide initiator and N-bromosuccinimide brominating agent is also taught in *Organic Syntheses*, Vol. 33, pp. 96–98 (1953). The use of various activators or initiators for the N-bromosuccinimide brominating agent is taught in Horner et al, *Newer Methods of Preparative Organic Chemistry*, Vol. III, Academic Press, New York, New York (1964), pp. 151–168. Peroxides and azobisisobutyronitrile as free radical initiators were discussed for the reaction producing brominated thiophenes. The article teaches that photoinitiation is unfavorable and particularly shows the effect of ultraviolet light which, although operative, is considerably less reactive and selective. Offermann et al, Synthesis, 272 (1977) teach brominating each methyl side-chain of 2,6-dimethylpyridine in the presence of light and an azobisisobutyronitrile initiator.

The recent advances in pharmaceutical uses for thiophene compounds as chemical intermediates and as building blocks in pharmaceutical compounds indicates a need for processes which will produce such intermediates without serious waste disposal problems, at reasonable cost and with as few undesirable by-products as possible. Such undesirable by-products produced by non-selective bromination processes cause impurity problems in the final intermediate and require extensive waste purification with the attendant problems of excessive cost of processing and equipment. Further, it is always desired to increase the productivity of given reaction equipment by increasing the yield, which also lowers the cost of such valuable pharmaceutical intermediates. It is particularly desired to increase the selectivity of the reaction for alkylating the side-chains, especially the lower alkyl side-chains, of heterocyclic compounds such as thiophenes. Accordingly, a process having the advantages described above would be extremely desirable. The process provided by the present invention realizes such advantages.

THE INVENTION

Many of the advantages of high selectivity, increased yield and lower process cost described above can be realized by providing a process according to the present invention, which process includes the bromination of the alkyl side-chain of an alkyl-substituted heterocyclic compound with a brominating agent selected from N-bromosuccinimide, 1,3-dibromo-5,5-dimethyl hydantoin and N-bromoacetamide in a solvent comprising carrying out said bromination in the presence of infrared light as an initiator for the free radical bromination reaction.

As indicated above, the process of the present invention can be employed to brominate the alkyl side-chain of alkyl-substituted heterocyclic compounds. The alkyl side-chain can have from 1 to about 4 carbon atoms and is preferably a saturated hydrocarbyl radical. Typical of such are methyl, ethyl, propyl and butyl radicals. Preferably, the alkyl radical is a methyl radical because of its presence in numerous compounds of interest as intermediates.

Typical of the heterocyclic compounds with which the brominated intermediate produced by the process of this invention can be useful are thiophene, furan, pyridine, 2-methylpyridine, lutidine, methylquinoline, dimethylfuran, dimethylthiophene and similar heterocyclic compounds. Preferably, for their interest as pharmaceutical intermediates, the thiophene compounds are of particular interest. Most preferred are 2- and 3-methylthiophene and most particularly preferred is 3-methylthiophene.

The above heterocyclic compounds, using the process of our invention, can be brominated by various conventional brominating agents. The use of N-bromosuccinimide is well documented. Other brominating agents include 1,3-dibromo-5,5-dimethyl hydantoin and N-bromoacetamide. Any well known brominating agent can be used. However, it has been found that 1,3-dibromo-5,5-dimethyl hydantoin and N-bromosuccinimide are preferred. Preferably, the molar ratio of brominating agent to starting alkyl-substituted heterocyclic compound is 1:1. However, it has been found that using the process of our invention an excess of starting alkyl-substituted heterocyclic compounds above stoichiometric can be employed to enhance the selectivity of the reaction. Thus, it is preferred that the molar ratio of the brominating agent to the starting alkyl-substituted heterocyclic compound is from 1:1 to about 1:3. More preferably, the molar ratio of brominating agent to, for example, an alkyl thiophene compound is about 1:2. When this molar ratio is employed, the selectivity of bromination on the alkyl side-chain is enhanced, the production of undesirable nuclear bromination products is decreased, and the valuable bromine compound is entirely used without serious losses of bromine while any excess starting compound can be recycled to another bromination reaction.

The bromination process with the present invention is preferably carried out in a solvent which facilitates the bromination. Prior art studies have shown that certain brominations take place with more facility in one solvent versus another. Preferably, the chlorinated solvents are employed. The investigation of the effects of solvent in the photochlorination of 2,3-dimethylbutane was studied in by Russell, *J. Amer. Chem. Soc.*, Vol. 80, pp. 4987-4996 (1958) and found that some solvents produced a solvent effect which facilitated one form of chlorination rather than another. A study of the solvents used in the process of the present invention indicates that chlorinated solvents such as chloroform, methylene chloride, 1,2-dichloroethane and bromobenzene do not show satisfactory results. Likewise, some non-chlorinated solvents such as methylformate and toluene give rather poor results with respect to selectivity of bromination on the alkyl side-chain. In contrast, aromatic solvents such as benzene, and cycloaliphatic solvents such as cyclohexane, show good selectivity. A preferred solvent for the process of this invention is carbon tetrachloride, which has long been known as an excellent solvent for bromination of alkyl thiophenes with various brominating agents. Such preferred solvents are non-polar and do not dissolve the brominating agents readily, having the effect of directing the bromination on the alkyl side-chain.

The relative amount of solvent to starting material also has a role to play in producing the advantageous results of the process of the present invention. Thus, as the concentration of starting alkyl-substituted heterocyclic compound in the solvent increases, the selectivity and yield of the side-chain bromination decrease. It is thus thought more advantageous to operate the process of the present invention under dilute conditions. It has been found that satisfactory selectivity and yield can be obtained by carrying out the process of the present invention with an initial concentration of the alkyl-substituted heterocyclic compound of 5 to about 20 percent by weight in the solvent. Preferably, the alkyl thiophenes can be satisfactorily and selectively brominated on the alkyl radical in carbon tetrachloride at a concentration of from 5 to about 10 percent by weight.

The time of reaction is only that necessary to complete the reaction and the reaction can be carried out generally at elevated temperatures, particularly, it is advantageous to carry out the reaction at reflux conditions under atmospheric pressure.

The selectivity of the reaction is highly dependent on the initiator employed. The prior art teaches that peroxide initiators, azobisisobutyronitrile and ultraviolet light initiators have been used with the photoinitiation by ultraviolet light being least preferred from selectivity and yield. In complete contrast to the teaching of the prior art, it has now been found that the use of infrared light as an initiator provides selectivity and yields as good as the peroxide and azobisisobutyronitrile initiators of the prior art. Thus, it is indeed surprising in view of the fact that ultraviolet light is less effective an initiator than the peroxides and azobisisobutyronitrile, that infrared light would be satisfactory and preferred initiator. Accordingly, the present invention provides an improved process for brominating 3-methylthiophene with a brominating agent selected from N-bromosuccinimide, 1,3-dibromo-5,5-dimethyl hydantoin and N-bromoacetamide in a suitable solvent in which the improvement is using infrared light as the initiator for the selective free radical bromination of the methyl side-chain on the 3-methylthiophene. The infrared light is considered to be that light having a wave length greater than 7,000 angstroms in the light spectra. Preferably, infrared light can be obtained from commercially available lamps which range in a wattage from 100–500 watts. Such lamps are commercially available from major manufacturers of electric lamps. It is only necessary for the light to be shined on the reaction mixture as conventionally practiced. Thus, the conventional methods for light catalyzed reactions can be used in the process of this invention. The improvement of using an infrared light source as an initiator is easily accomplished by conventional methods. The number and wattage of infrared sources or lamps employed and the time period of irradiation can be readily determined by varying the examples of the process of this invention.

In general, the process of this invention can be carried out by placing the solvent, the brominating agent and alkyl-substituted heterocyclic compound in the reaction vessel, heating the mixture to reflux and turning on the source(s) of infrared light so that the infrared light is incident on the reaction mixture. The reaction proceeds in relatively short time and the infrared light source is turned off. The reaction mixture is cooled and the product separated. The improved process of the present invention is more thoroughly illustrated in the following examples.

EXAMPLES 1-5

The following examples were run to show the comparison between the brominating selectivity and reactivity of various initiators for the bromination of 3-methylthiophene with N-bromosuccinimide. The brominations were run on an equivalent basis with the only variable being the initiator. However, the nature of the initiators require that two methods be used for the reaction, as follows:

Method A: To a refluxing solution of 3-methylthiophene (1.0 mole) in carbon tetrachloride (800 ml) were added portionwise over ten minutes N-bromosuccinimide (1 mole) and in, different reaction vessels for different initiators, 2 mole % of azobisisobutyronitrile, lauroyl peroxide and benzoyl peroxide. After the addition of the brominating agent was completed, the reaction vessel was cooled and the solution filtered to remove the succinimide formed. The analyses by vapor phase chromatography of the resultant solutions in each run are given in Table 1.

Method B: In separate runs, a stirred mixture of 3-methylthiophene (1.0 mole), N-bromosuccinimide (1.1 mole) and carbon tetrachloride (800 ml) was refluxed under illumination from a 250-watt General Electric Industrial Reflector lamp or a 2.5-watt ultraviolet lamp, respectively, for about 18 minutes. The resultant solution was filtered to remove the succinimide formed. The analysis of the product in each run by vapor phase chromatography is given in Table 1.

In Table 1, the following abbreviations have been used:

| Abbreviation | Meaning |
|---|---|
| 3-MT | 3-Methylthiophene |
| 3-TB | 3-Thenylbromide |
| 2B-3MT | 2-Bromo-3-methylthiophene |
| 2B-3TB | 2-Bromo-3-thenylbromide |
| 3-TDB | α,α-Dibromo-3-methylthiophene |

TABLE I

Bromination of 3-Methylthiophene
Effect of Initiator

| Ex. No. | Initiator | % Yield of Brominated Thiophenes | | | | |
|---|---|---|---|---|---|---|
| | | 3-TB | 2B-3MT | 2B-3TB | 3-TDB | Other |
| 1 | Azobisisobutyronitrile | 78 | 4 | — | 3 | — |
| 2 | Lauroyl peroxide | 69 | 8 | 2 | 1 | 1 |
| 3 | Benzoyl peroxide | 70 | 9 | 3 | 3 | 2 |
| 4 | Sunlamp (infrared light) | 75 | 1 | 1 | 16 | — |
| 5 | Ultraviolet light | 2 | 82 | <1 | — | 6 |

From the results above, it is clear that peroxide and ultraviolet light initiators are less satisfactory from both yield and selectivity considerations. Further, although the azobisisobutyronitrile initiator was slightly better than infrared light, it had higher amounts of ring brominated thiophene derivatives. The large amount of dibrominated side-chain material produced using the infrared initiator indicates the reaction was completed before the illumination time was over and a shorter reaction time could have been used.

The next series of examples illustrates the effect of the concentration of the starting material, as illustrated by 3-methylthiophene, on the bromination reaction using an infrared light initiator for the side-chain bromination reaction.

EXAMPLES 6–8

Following the general procedure of Example 4 (Method B), a stirred mixture of 3-methylthiophene (98 g, 1 mole), N-bromosuccinimide (195.8 g, 1.1 mole) and carbon tetrachloride was refluxed under illumination from a 250-watt General Electric Industrial Reflector lamp for twenty minutes. Three runs were made in which the initial concentration of 3-methylthiophene in carbon tetrachloride was 12.5, 8.33 and 6.25 weight percent. After cooling and filtering to remove the succinimide, the resultant solution was analyzed by vapor phase chromatography and the results are given in Table 2 as follows:

TABLE 2

Bromination of 3-Methylthiophene
Solvent Dilution Effect

| Ex. No. | Wt % of 3MT in CCl₄ | % Yield of Brominated Thiophenes | | | | |
|---|---|---|---|---|---|---|
| | | 3-TB | 2B-3MT | 2B-3TB | 3-TDB | Other |
| 6 | 12.5 | 72 | 3 | — | 17 | 1 |
| 7 | 8.33 | 79 | 2 | — | 13 | — |
| 8 | 6.25 | 83 | 1 | — | 8 | 1 |

From the table, it is clear that as the initial concentration of 3-methylthiophene decreases from 12.5 weight percent to 6.25 weight percent, the yield and selectivity of the bromination on the methyl side-chain of the thiophene group increases significantly.

EXAMPLE 9

This example illustrates the unfavorable effect that a solvent can have on the yield and selectivity of the bromination reaction. Following the procedure of Examples 6–8, a stirred mixture of 3-methylthiophene (98.0 g, 1.0 mole), N-bromosuccinimide (195.7, 1.1 mole) and toluene (500 ml) was refluxed under illumination with a 250-watt General Electric Industrial Reflector lamp for twenty minutes. After cooling and filtering, the analysis by vapor phase chromatography showed 11% 3-thenylbromide, 64% 2-bromo-3-methylthiophene, less than 1% 2-bromo-3-thenylbromide and 4% other brominated thiophenes.

EXAMPLE 10

This example illustrates the effect of excess starting material. A stirred mixture of 3-methylthiophene (196 g, 2 moles), N-bromosuccinimide (178 g, 1 mole) and carbon tetrachloride (1176 ml) was refluxed under illumination of a 250-watt General Electric Industrial Reflector lamp for fifteen minutes. The solution was then cooled and filtered. A sample was analyzed by vapor phase chromatography to contain 89% 3-thenyl bromide, less than 1% 2-bromo-3-methylthiophene and 5% α,α-dibromo-3-methylthiophene.

EXAMPLE 11

This example illustrates the use of 1,3-dibromo-5,5-dimethyl hydantoin as the brominating agent. A stirred mixture of 3-methylthiophene (24.5 g, 0.25 mole), 1,3-dibromo-5,5-dimethyl hydantoin (28.59 g, 0.1 mole) and carbon tetrachloride (300 ml) was refluxed under illumination of a 250-watt General Electric Industrial Reflector lamp for about 9 minutes. A solution color change from buff to orange was noted immediately when the lamp was turned on. The reaction was then cooled and filtered. A vapor phase chromatography analysis indicated the following % Yield: 69.3% 3-thenylbromide, 2.5% 2-bromo-3-thenylbromide and 17.3% 2-bromo-3-methylthiophene.

EXAMPLE 12

This example illustrates the bromination of alkyl-substituted furan. A stirred mixture of 2-methylfuran (8.2 g, 0.1 mole), N-bromosuccinimide (17.8 g, 0.1 mole) and carbon tetrachloride (73.8 g) was refluxed under illumination of a 250-watt General Electric Industrial Reflector lamp for 30 minutes. The reaction mixture was then cooled and filtered. Analysis with proton NMR using 1,1,2,2-tetrachloroethane as an internal standard gave 73% yield of 2-bromomethylfuran and 2% yield of 2,2-dibromomethylfuran.

EXAMPLE 13

This example illustrates the bromination of alkyl-substituted pyridine. A stirred mixture of 2,6-dimethylpyridine (10.7 g, 0.1 mole), N-bromosuccinimide (35.6 g, 0.2 mole) and carbon tetrachloride (96.3 g) was refluxed under illumination from a 250-watt General Electric Industrial Reflector lamp for 4 hours. Then the reaction mixture was cooled and filtered. Analysis of the carbon tetrachloride solution with proton NMR showed 24% yield of 2,6-bis(bromomethyl)-pyridine, 15% yield of 2-bromomethyl-6-methylpyridine, and 28% yield of 2,2-dibromo-6-methylpyridine.

Having illustrated the process of the invention, one skilled in the art can readily envision changes and modifications within the scope and spirit of the invention. Therefore, it is desired that the invention be limited only by the lawful scope of the following claims.

What is claimed is:

1. A process for the selective bromination on an alkyl side-chain of an alkyl heterocyclic compound with a brominating agent selected from N-bromosuccinimide, 1,3-dibromo-5,5-dimethyl hydantoin and N- bromoacetamide in a solvent comprising carrying out said bromination in the presence of infrared light as an initiator for the free radical bromination reaction.

2. The process of claim 1 further characterized in that said bromination reaction is carried out at elevated temperature.

3. The process of claim 1 wherein said alkyl sidechain is an alkyl radical selected from methyl, ethyl, propyl and butyl radicals.

4. The process of claim 1 wherein said alkyl heterocyclic compound is selected from an alkyl thiophene, an alkyl pyridine or an alkyl furan.

5. The process of claim 4 wherein said alkyl heterocyclic compound is an alkyl thiophene.

6. The process of claim 4 wherein said alkyl thiophene is a methyl thiophene.

7. The process of claim 4 wherein said alkyl thiophene is 3-methylthiophene.

8. The process of claim 7 further characterized in that the initial concentration of 3-methyl thiophene ranges from about 5 to about 20 percent by weight in said solvent.

9. The process of claim 7 further characterized in that the initial concentration of 3-methyl thiophene ranges from about 5 to about 10 percent by weight in said solvent.

10. The process of claim 7 further characterized in that the molar ratio of said brominating agent to said 3-methylthiophene is from 1:1 to about 1:3.

11. The process of claim 7 further characterized in that the molar ratio of brominating agent to 3-methylthiophene is about 1:2.

12. The process of claim 7 further characterized in that the initial concentration of 3-methylthiophene is from about 5 to about 20 percent by weight in said solvent and the molar ratio of said brominating agent to said 3-methylthiophene is from 1:1 to about 1:3.

13. The process of claim 7 further characterized in that the initial concentration of 3-methylthiophene in said solvent is from about 5 to about 20 percent by weight and the molar ratio of said brominating agent to said 3-methylthiophene is about 1:2.

14. The process of claim 7 further characterized in that the initial concentration of 3-methylthiophene in said solvent is from about 5 to about 10 percent by weight in said solvent and the molar ratio of said brominating agent to said 3-methylthiophene is from about 1:1 to about 1:3.

15. The process of claim 7 further characterized in that the initial concentration of said 3-methylthiophene in said solvent is from about 5 to about 10 percent by weight and the molar ratio of said brominating agent to said 3-methylthiophene is about 1:2.

16. The process of claim 7 further characterized in that said bromination reaction is carried out at elevated temperature, the initial concentration of said 3-methylthiophene in said solvent is from about 5 to about 10 percent by weight and the molar ratio of said brominating agent to said 3-methylthiophene is about 1:2.

17. The improved process of claim 7 further characterized in that the 3-methylthiophene and brominating agent are mixed together, the reaction mixture is heated to its reflux temperature, the reaction mixture is illuminated by the source of infrared light for a period sufficient to initiate the bromination reaction and maintained until the reaction is substantially complete.

* * * * *